US010010705B2

(12) United States Patent
Greenhalgh et al.

(10) Patent No.: US 10,010,705 B2
(45) Date of Patent: Jul. 3, 2018

(54) POWDER DELIVERY DEVICE

(75) Inventors: Paul Greenhalgh, Cambridge (GB); Eliane Schutte, Leiden (NL)

(73) Assignee: Mallinckrodt Pharma IP Trading D.A.C., Dublin (IE)

(*) Notice: Subject to any disclaimer, the term of this patent is extended or adjusted under 35 U.S.C. 154(b) by 1075 days.

(21) Appl. No.: 13/995,267

(22) PCT Filed: Dec. 23, 2011

(86) PCT No.: PCT/GB2011/052586
§ 371 (c)(1), (2), (4) Date: Jun. 18, 2013

(87) PCT Pub. No.: WO2012/085600
PCT Pub. Date: Jun. 28, 2012

(65) Prior Publication Data
US 2013/0274690 A1 Oct. 17, 2013

(30) Foreign Application Priority Data
Dec. 23, 2010 (GB) .................................. 1021881.6

(51) Int. Cl.
*A61M 35/00* (2006.01)
*A61M 11/06* (2006.01)

(52) U.S. Cl.
CPC .......... *A61M 35/003* (2013.01); *A61M 11/06* (2013.01); *A61M 2202/064* (2013.01)

(58) Field of Classification Search
CPC ................ A61M 11/06; A61M 35/003; A61M 2202/064; A61M 5/30; B05B 1/28
See application file for complete search history.

(56) References Cited

U.S. PATENT DOCUMENTS 2,151,418 A 3/1939 Bolte
2,501,279 A 3/1950 Kark
4,620,847 A 11/1986 Shishov et al.
4,711,056 A * 12/1987 Herrington ............. B24C 1/045 451/102
5,273,531 A * 12/1993 Knoepfler ............. A61M 31/00 604/212
5,366,122 A 11/1994 Guentert et al.
5,584,807 A * 12/1996 McCabe ................ C12M 35/00 604/24
5,702,373 A * 12/1997 Samson .............. A61M 25/005 604/526
5,884,621 A 3/1999 Matsugi et al.
(Continued)

FOREIGN PATENT DOCUMENTS

CN 201216785 Y 4/2009
DE 619625 C 10/1935
(Continued)

*Primary Examiner* — Theodore Stigell

(57) ABSTRACT

Provided is a device for the dispensing of powders of the type in which a generated gas flow entrains the powder to be dispensed and carries the powder from the device via a barrel. The barrel has a bore including a main portion with a continuous internal surface, and is characterized in that the length of the main portion is at least fifteen times its maximum internal diameter; and/or the internal bore of the main portion is tapered; and/or the barrel has an outwardly flared outlet portion.

20 Claims, 9 Drawing Sheets

(56) References Cited

U.S. PATENT DOCUMENTS

| | | | | | |
|---|---|---|---|---|---|
| 5,951,531 | A * | 9/1999 | Ferdman | A61M 11/02 604/24 |
| 6,024,129 | A | 2/2000 | Schima | |
| 6,053,889 | A * | 4/2000 | Heinzen | C12M 35/00 604/24 |
| 6,168,587 | B1 * | 1/2001 | Bellhouse | A61M 5/3015 604/522 |
| 6,261,258 | B1 | 7/2001 | Saines | |
| 6,344,027 | B1 * | 2/2002 | Goll | A61B 17/32037 604/68 |
| 6,971,384 | B2 | 12/2005 | Gieschen et al. | |
| 7,025,056 | B2 | 4/2006 | Eason et al. | |
| 7,060,048 | B1 * | 6/2006 | Nat | A61M 5/3015 604/500 |
| RE43,824 | E * | 11/2012 | Sheldrake | A61M 5/3015 604/68 |
| 8,721,582 | B2 * | 5/2014 | Ji | A61M 13/00 604/216 |
| 2002/0000477 | A1 * | 1/2002 | Hara | B05B 7/0475 239/104 |
| 2005/0205087 | A1 | 9/2005 | Kablik et al. | |
| 2007/0160543 | A1 | 7/2007 | Moller | |
| 2011/0230820 | A1 | 9/2011 | Lillis et al. | |
| 2011/0313357 | A1 * | 12/2011 | Skutnik | A61M 5/14248 604/151 |

FOREIGN PATENT DOCUMENTS

| | | | |
|---|---|---|---|
| EP | 1477119 | A1 | 11/2004 |
| EP | 1607117 | A1 | 12/2005 |
| FR | 2863503 | A1 | 6/2005 |
| GB | 472355 | A | 9/1937 |
| GB | 539351 | A | 9/1941 |
| GB | 572015 | A | 9/1945 |
| GB | 572112 | A | 9/1945 |
| GB | 607237 | A | 8/1948 |
| GB | 628675 | A | 9/1949 |
| GB | 668341 | A | 3/1952 |
| GB | 808273 | A | 2/1959 |
| GB | 878106 | A | 9/1961 |
| WO | 9209322 | A1 | 6/1992 |
| WO | 9503846 | A1 | 2/1995 |
| WO | 2005037443 | A2 | 4/2005 |
| WO | 2006044800 | A2 | 4/2006 |
| WO | 2008106616 | A2 | 9/2008 |
| WO | 2010070333 | A2 | 6/2010 |

* cited by examiner

POWDER DELIVERY DEVICE

TECHNICAL FIELD

This invention relates to improvements in a device for the dispensing of powder. In particular, the invention relates to an improvement in devices of the general type disclosed in International Patent Application WO2010/070333 (which is hereby incorporated by reference). Such devices are of particular utility in surgical procedures or other medical applications, for the topical delivery of powder to an internal or external surface of the body.

BACKGROUND

In devices of the type disclosed in WO2010/070333, a flow of gas entrains powder that is to be dispensed and carries that powder out of the device via a barrel. The barrel serves to direct the powder to the desired application site. In the devices illustrated in WO2010/070333, the barrels are rather short and are of simple construction.

BRIEF SUMMARY

It has now surprisingly been found that the performance of devices of the type disclosed in WO2010/070333 may be substantially improved by modifications to the design of the barrel. In particular, elongation of the barrel and/or the incorporation of certain structural features in the internal bore of the barrel lead to improvements.

Thus, according to the invention there is provided a device for the dispensing of powder, the device being of the type in which a generated gas flow entrains the powder to be dispensed and carries the powder from the device via a barrel, the barrel having a bore including a main portion with a continuous internal surface, characterized in that:

(a) the length of the main portion is at least fifteen times its maximum internal diameter; and/or (b) the internal bore of the main portion is tapered; and/or (c) the barrel has an outwardly flared outlet portion.

The device according to the invention is advantageous in that the form of the barrel may lead to certain improvements in performance. In particular, the form of the barrel may be chosen in such a way that the shape of the plume of powder emitted from the device is optimised for a particular application. Thus, the distribution of powder on the intended site of application may be made more uniform. In addition, the velocity of the powder plume may be increased, and this may result in the form of the plume being maintained over greater distances, so that the powder plume remains intact when projected over larger distances than those obtained with a conventional device, enabling the powder delivery device to be held a greater distance from the desired delivery site. This may be advantageous, for instance, in surgical procedures where it may not be possible to hold the device close to the intended site of application of the powder. In addition, fall-off of powder from the plume, under the influence of gravity, may be reduced, leading to reduced deposition of powder at undesired locations. In addition, the outlet may be less prone to clogging, improving performance and reducing the maintenance required. Dispersion of the powder as it leaves the device may also be improved. In general, the device according to the invention may operate effectively over a wide range of gasflow pressures, e.g., from about 0.5 bar to about 7 bar, though for most applications pressures in the range 0.5 bar to 2 bar are generally satisfactory, e.g., from 0.5 bar to 1.5 bar.

In some preferred embodiments of the device, the length of the main portion is at least fifteen times its maximum internal diameter; and the internal bore of the main portion is tapered.

In other embodiments of the device, the barrel has an outwardly flared outlet portion.

In some particularly preferred embodiments of the device:

(a) the length of the main portion is at least fifteen times its maximum internal diameter; and (b) the internal bore of the main portion is tapered; and (c) the barrel has an outwardly flared outlet portion.

In embodiments in which the barrel is elongated, the barrel may be rigid or it may be flexible.

In rigid embodiments, the length of the main portion of the barrel is at least fifteen times, e.g., at least eighteen times or at least twenty times, its maximum internal diameter, or more.

In rigid embodiments, the length of the main portion is typically between about 30 mm and 100 mm, e.g., about 50 mm or about 75 mm. The maximum internal diameter of the main portion is typically from 1 mm to 6 mm, e.g., about 2 mm or about 3 mm.

In flexible embodiments of the barrel, the barrel is generally longer than for rigid embodiments, the length of the main portion of the barrel typically being between about 50 mm and about 300 mm, more commonly between about 50 mm and about 200 mm, and typically between about 100 mm and 180 mm, e.g., about 150 mm. The internal diameter of the barrel in such embodiments is most commonly between about 1 mm and about 6 mm, typically between about 1.5 mm and about 4 mm, e.g., about 2 mm or about 3 mm.

In order for the barrel to be flexible, its main portion is typically formed as a plastics tube, the plastics material being such that the tube may be manually deformed to the required shape without occlusion of the internal bore. The nature of the required shape will generally be dictated by the circumstances of the procedure in which the device is being used. Most commonly, a single bend may be introduced into the barrel by the user of the device, but in other situations it may be necessary to form the barrel into a more complex shape, e.g., with a double bend (i.e. an "S"-shape or the like). It has surprisingly been found that, even when bent into shapes as extreme as are ever likely to be required in practice (e.g., two 90° bends), the pattern of powder dispensed from the device can remain satisfactory in terms of the geometry of the plume of powder emerging from the distal end of the barrel and the pattern of deposition of the powder.

The nature of the plastics material from which the flexible elongate barrel is formed may be such that the tube retains the shape into which it is deformed, at least for as long as is required during normal use. Preferably, however, the barrel incorporates one or more malleable elongate members that can be readily deformed, and which have the effect of retaining the barrel in the desired configuration until it is once again manually deformed to another configuration. Such members may take the form of wires or rods of metal or other malleable material that are incorporated into the barrel. Most commonly, such wires or rods are disposed parallel to the longitudinal axis of the barrel. In some embodiments, the main portion of the barrel is a tube having more than one lumen, one lumen (normally the one having the greatest cross-sectional area) constituting the bore of the barrel along which powder is dispensed, and at least one lumen accommodating one or more wires or rods. In other embodiments, one or more wires or rods are embedded in the plastics material from which the barrel is formed. There may be just one such wire or rod, or there may be two, three, four or more such wires. Where there is more than one wire or rod, those wires or rods are most commonly equiangularly spaced around the main portion of the barrel.

Forms of material that are suitable for the malleable wires or rods are copper wire and copper-coated steel wire. In one currently preferred embodiment, a single such wire is embedded in the wall of the tube that constitutes the main portion of the barrel. In other embodiments, two, three or four such wires may be used.

In other embodiments, another form of malleable material may be used to enable the form of the barrel to be altered. For instance, the main portion of the barrel may be provided, along the whole or part of its length, with a sheath of material that holds its shape when deformed, e.g., a foam material of the type known as memory foam or visco-elastic foam.

In embodiments in which the internal bore of the main portion is tapered, the internal diameter of the bore may decrease from the upstream to the downstream end of the main portion, i.e., the internal bore of the main portion may converge. Alternatively, the internal diameter of the bore may increase from the upstream to the downstream end of the main portion, i.e., the internal bore of the main portion may diverge. The taper angle may typically be in the range 0.5° to 3°, more commonly 0.5° to 2°.

Embodiments in which the main portion of the barrel is flexible typically have a main portion that is considerably longer than is the case for rigid embodiments. Those flexible embodiments are typically formed by extrusion and in such cases will therefore have an internal bore of constant cross-section. Embodiments in which the main portion of the barrel is rigid are more commonly formed by injection moulding, in which case the internal bore of the main portion of the barrel may have a uniform cross-section or may, more preferably, be tapered.

In embodiments in which the barrel has an outwardly flared outlet portion, the outlet portion typically has a length of between 5 mm and 25 mm, more commonly between 5 mm and 10 mm. The internal diameter of the outlet portion may increase from its upstream to its downstream end by a factor of two or more. As will be readily appreciated, where the outlet portion is "flared", that term refers to the internal shape of the outlet, i.e., to a widening of the outlet from its upstream to its downstream end. That widening may or may not be reflected in the external shape of the outlet.

Apart from the modifications to the barrel described above, the device according to the invention may be as described in WO2010/070333, in particular in relation to FIGS. 3 to 12 of that document. Briefly summarised, such a device has a main body that may comprise upper and lower housing components formed in plastics material by injection moulding. The main body may have the general form of an elongate cylinder that is adapted to be held in a user's hand, the underside of the lower component being shaped to facilitate such grip. A push button-type actuator may be mounted in the top of the main body such that, when the device is held by the user, the actuator can be depressed by the thumb of the hand that holds the device. A flexible tube may extend from the rear end of the device and may be adapted to be connected to a gas source, e.g., a source of compressed air. A connector may be provided at the distal end of the tube. A vial containing the powder that is to be dispensed from the device may be coupled to the device, e.g., via an upstanding spigot that is received within the mouth of the vial. The barrel may extend from the front end of the device.

The barrel may be provided with a mounting that enables its orientation relative to the main body of the device of which it forms part to be varied. For instance, the barrel may engage the main body of the device in the manner of a ball-and-socket connector, so that the orientation of the barrel may be adjusted, e.g., manually by the operator.

In presently preferred embodiments, however, the barrel is connected to the main body of the device in a fixed orientation. The barrel may be connected to the main body by a threaded connection, or by a suitable quick release connection such as a bayonet fitting. Other forms of connection may alternatively be used, e.g., a luer lock-type connection, or an interference fit or the like.

The device according to the invention may be manufactured using medical grade materials, most components being most conveniently manufactured in plastics by techniques such as injection moulding and extrusion. Where appropriate, components may be manufactured in other materials, e.g., glass or metal.

The device according to the invention may be used to deliver a wide variety of powders to a surface of the body. Such powders include agents intended to have a therapeutic effect, either in terms of a pharmacological effect on the body or as disinfectants or the like useful in the prevention or treatment of infections. One particular field in which the device of the invention is useful, however, is for the delivery of haemostatic powder compositions to internal tissues exposed during surgical procedures or after traumatic injury. Such haemostatic compositions, which may also be described as tissue sealants, may for instance comprise dry powder mixtures of fibrinogen and thrombin. Such a mixture is essentially inert when formulated in the dry state, but once hydrated, e.g., upon application to a bleeding wound, the mixture leads to the production of fibrin which cross-links to form a blood clot.

Thus, according to a further aspect of the invention, there is provided a method of delivering a haemostatic composition to an internal tissue exposed during surgical procedures or after traumatic injury, which method comprises providing a device as described above, which device is charged with a quantity of a haemostatic composition in dry powder form, and dispensing said composition from said device onto said tissue.

BRIEF DESCRIPTION OF DRAWINGS

The invention will now be described in greater detail, by way of illustration only, with reference to the accompanying drawings, in which.

DETAILED DESCRIPTION OF THE EMBODIMENTS

Figure 1:
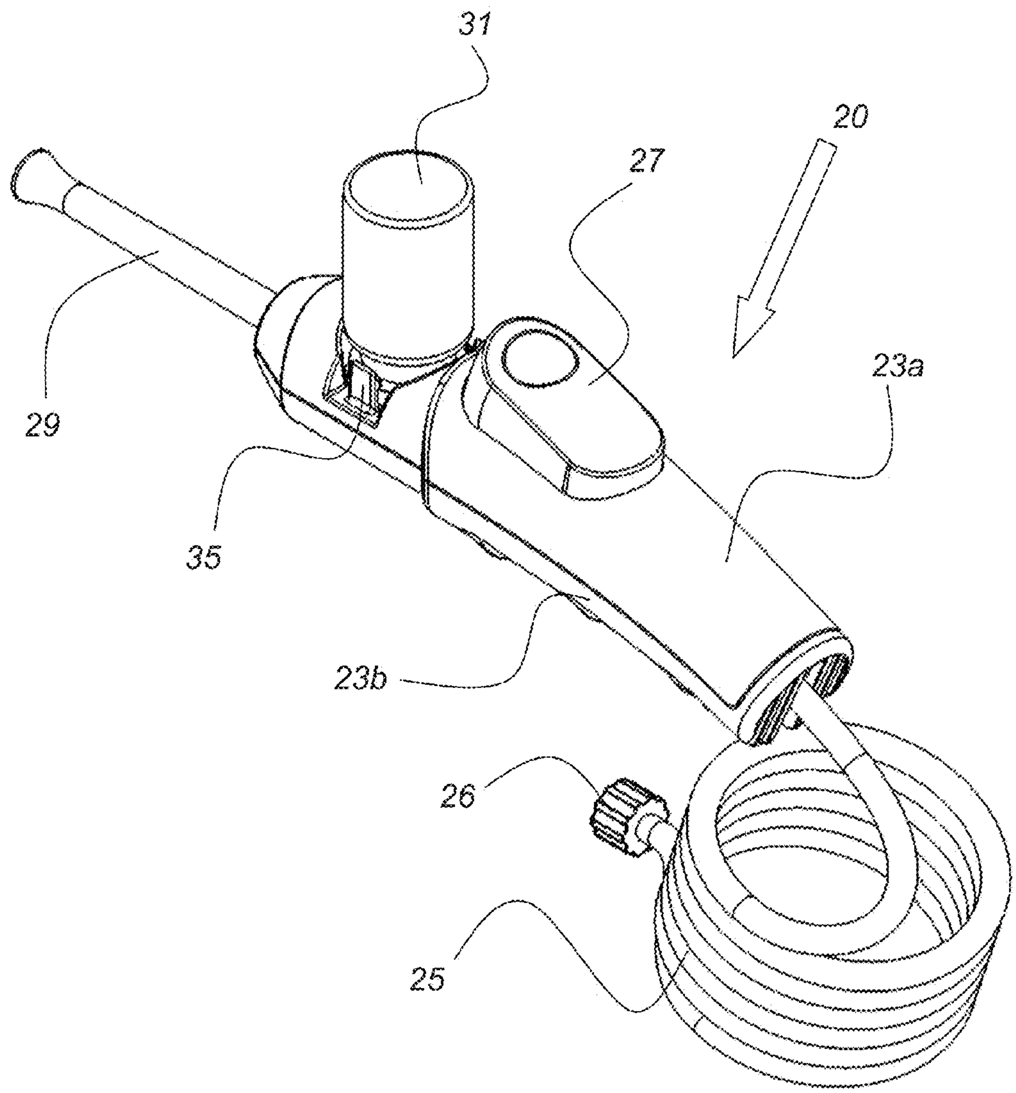
FIG. 1 is a perspective view of a first embodiment of a powder delivery device according to the invention.
Figure 2:
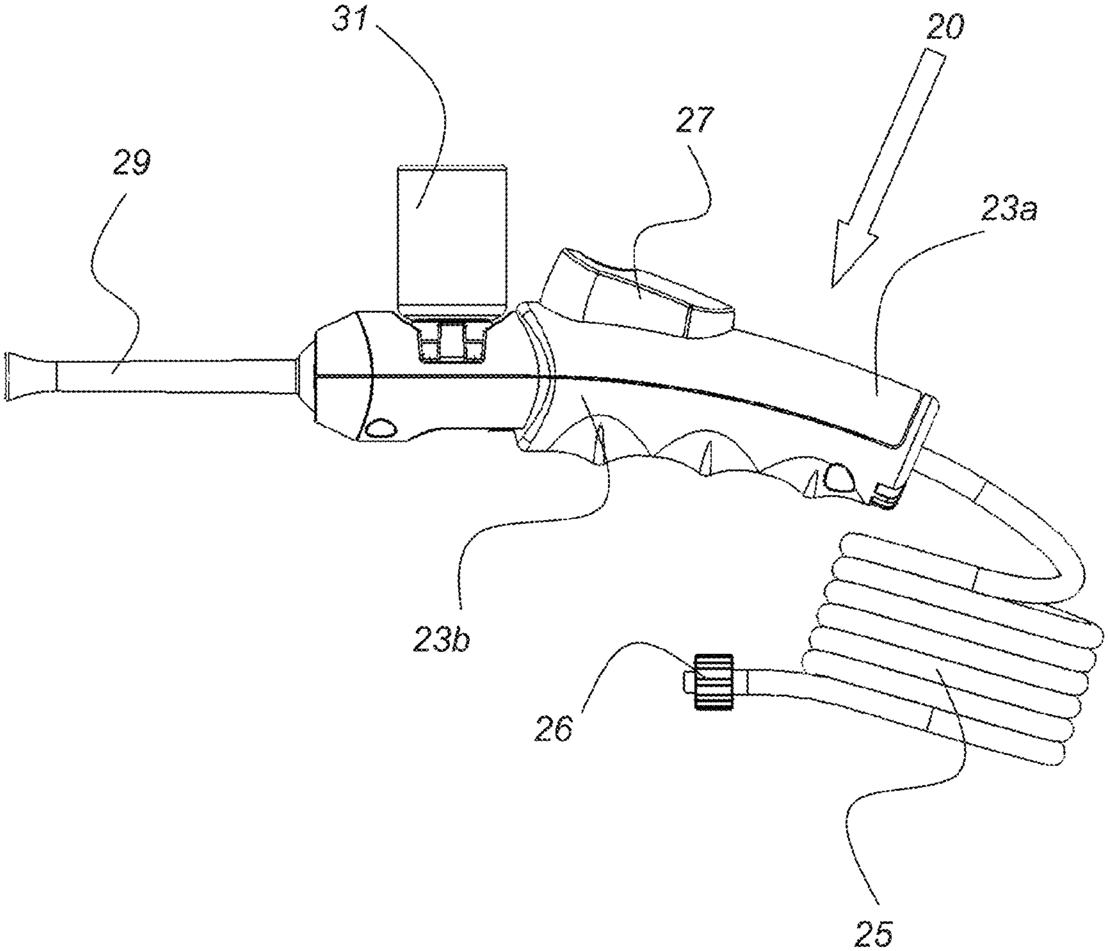
FIG. 2 is a side view of the device of FIG. 1.

Referring first to FIGS. 1 and 2, a first embodiment of a powder delivery device in accordance with the invention is generally designated 20. Save for the inventive modification described in greater detail below, the device 20 is of similar form to the device illustrated in FIGS. 3 to 12 of WO2010/070333. Briefly summarised, the device 20 has a main body that comprises upper and lower housing components 23*a*, 23*b* that are formed in plastics material by injection moulding. The main body has the general form of an elongate cylinder that is adapted to be held in a user's hand, the underside of the lower component 23*b* being shaped to facilitate such grip. A push button-type actuator 27 is mounted in the top of the main body such that, when the device 20 is held by the user, the actuator 27 can be depressed by the thumb of the hand that holds the device 20.

A flexible tube 25 extends from the rear end of the device 20 and is adapted to be connected to a gas source, e.g., a source of compressed air (not shown). A suitable connector 26 is provided at the distal end of the tube 25.

A glass vial 31 is coupled to the device 20 via an upstanding spigot (not visible) that is received within the mouth of the vial 31. A pair of clips 35 engages with a peripheral lip of the vial 31, so as to hold it securely in place. In other embodiments, the vial 31 may simply engage the spigot or similar formation with an interference fit and/or the spigot or similar formation may have a degree of resilience enabling a clip-type fitting to the vial. To facilitate sealing engagement of the vial 31 with the device 20, the formation that receives the mouth of the vial 31 may incorporate or be formed from a suitable elastomeric material (e.g., a thermoplastic elastomer). A device 20 having such a fitting may be produced using a two-shot molding process.

As for the device described in WO2010/070333, the front end of the device 20 is provided with a tubular barrel 29, through which powder is dispensed from the device 20. The barrel 29 in the present invention, however, is rather different in form to that described in the earlier patent application, as is discussed in greater detail below.

The base of the spigot with which the vial 31 is engaged is closed by a perforated plate, such that when the device is in the operative orientation shown in FIGS. 1 and 2, powder contained within the vial 31 rests upon the perforated plate. When the actuator 27 is depressed, gas is caused to flow through the device 20, as described in WO2010/070333. The flow of gas has two, related, effects. First, the gas flow drives a mechanical agitator in the form of a ball that is held captive within a circular track; rotation of the ball around the track induces vibrations in the device 20, the effect of which is to dislodge powder from the vial 31, through the perforated plate that constitutes the base of the spigot that is engaged by the vial 31. Secondly, a proportion of the gas flow is directed at the underside of the perforated plate, entrains the powder that is dislodged from the vial 31 and carries it from the device 20 via the barrel 29.

Thus, to dispense powder from the device 20, the user holds the device 20 in one hand, directs the barrel 29 at the intended site of application of the powder, and depresses the actuator 27 with the thumb. This permits gas to flow through the device 20, causing the ball to rotate rapidly around the track and inducing a degree of mechanical vibration that is transmitted to the vial 31. Most of the gasflow is vented from the device 20. However, a small proportion of gas is directed at the underside of the perforated plate. The mechanical agitation of the device 20 caused by rotation of the ball within the track facilitates the release of powder from the vial 31. The powder is entrained in the flow of air that escapes from the device 20 via the barrel 29. The powder is blown out of the device 1 and deposited on the site of application.

As noted above, the device 20 differs from that disclosed in WO2010/070333 in the form of the barrel 29. The barrel 29 is shown in FIGS. 3 and 4.

Figure 3:
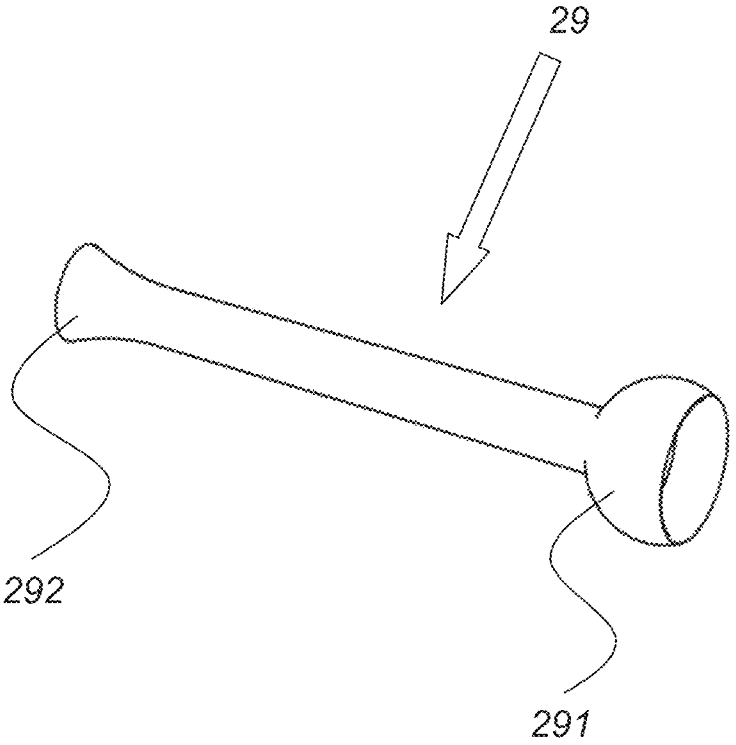
FIG. 3 shows a barrel that forms part of the device of FIG. 1.

As can be seen in FIG. 3, the barrel 29 is elongate and of circular cross-section, extending from a ball-type connector 291 at one end to a flared outlet 292 at the other. The ball-type connector 291 is captivated within an opening at the front of the main body of the device 20, between the upper and lower housing components 23*a*, 23*b*, in the manner of a ball-and-socket joint.

Figure 4:
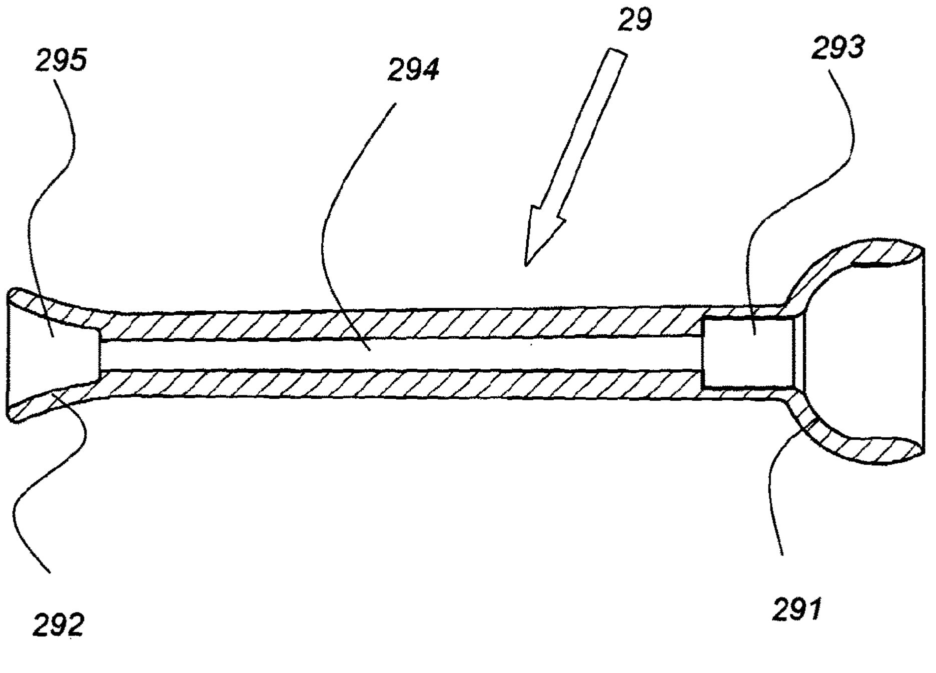
FIG. 4 is a cross-sectional view of the barrel of FIG. 3.

As can be seen from FIG. 4, the barrel 29 has an internal bore having an entry portion 293 that is of constant diameter, a main bore 294 that is of reduced diameter relative to the entry portion 292, and an outlet portion 295 within the flared outlet 292. The diameter of the main bore 294 reduces along its length.

The overall length of the barrel 29 is approximately 70 mm. The entry portion 293 of the internal bore has a diameter of approximately 5 mm and a length of approximately 8 mm. The diameter of the main bore 294, which has a length of approximately 48 mm, reduces from approximately 3.5 mm adjacent the entry portion 293 to approximately 2 mm where the main bore 294 meets the outlet portion 295. The angle of convergence of the internal wall of the main bore 294 relative to its longitudinal axis is thus approximately 1°.

The entry portion 293 receives a tube (not visible in the drawings) by which the gasflow and entrained powder are fed from the main body of the device 20 to the barrel 29.

The narrowing of the main bore 294 may cause an increase in velocity of the gasflow as it exits the device 20 and, together with the flared form of the outlet portion 295, this may help to maintain the shape of the powder plume emitted from the device 20, resulting in good coverage of the application site with powder. Fall off of powder from the emitted plume, under the influence of gravity, may be reduced, minimising the amount of powder that is dispensed onto sites other those to which the powder is intended to be delivered. The flared form of the outlet portion 295 also leads to a reduced likelihood of clogging.

Figure 5A:
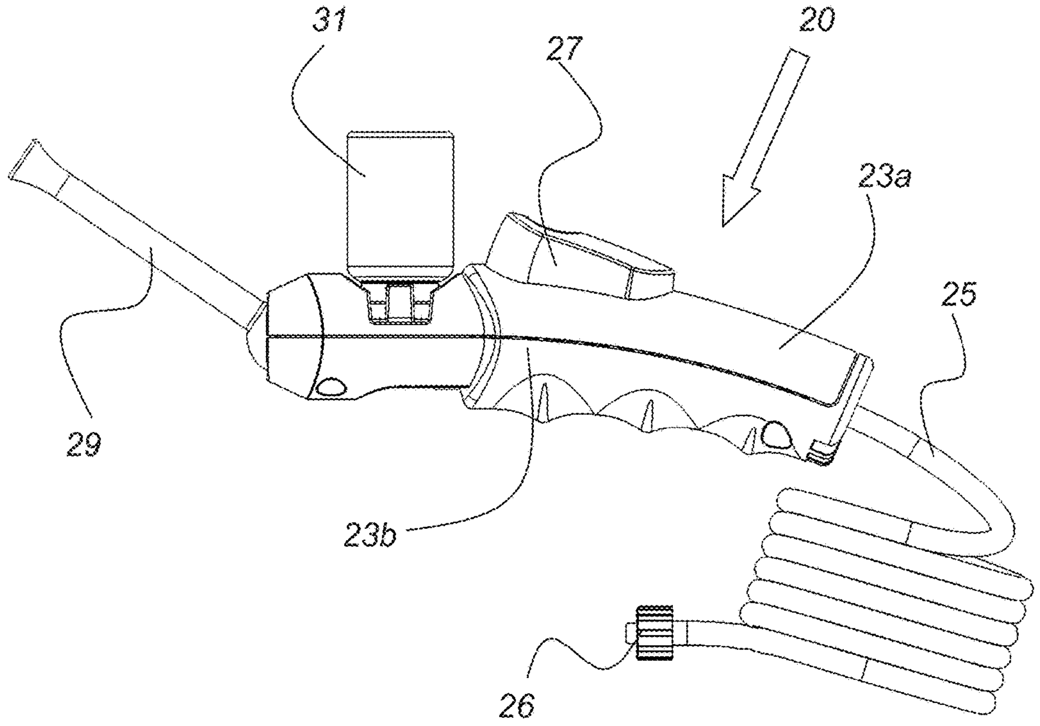
FIGS. 5(*a*) and (*b*) illustrate the range of vertical movement of the barrel.
Figure 5B:
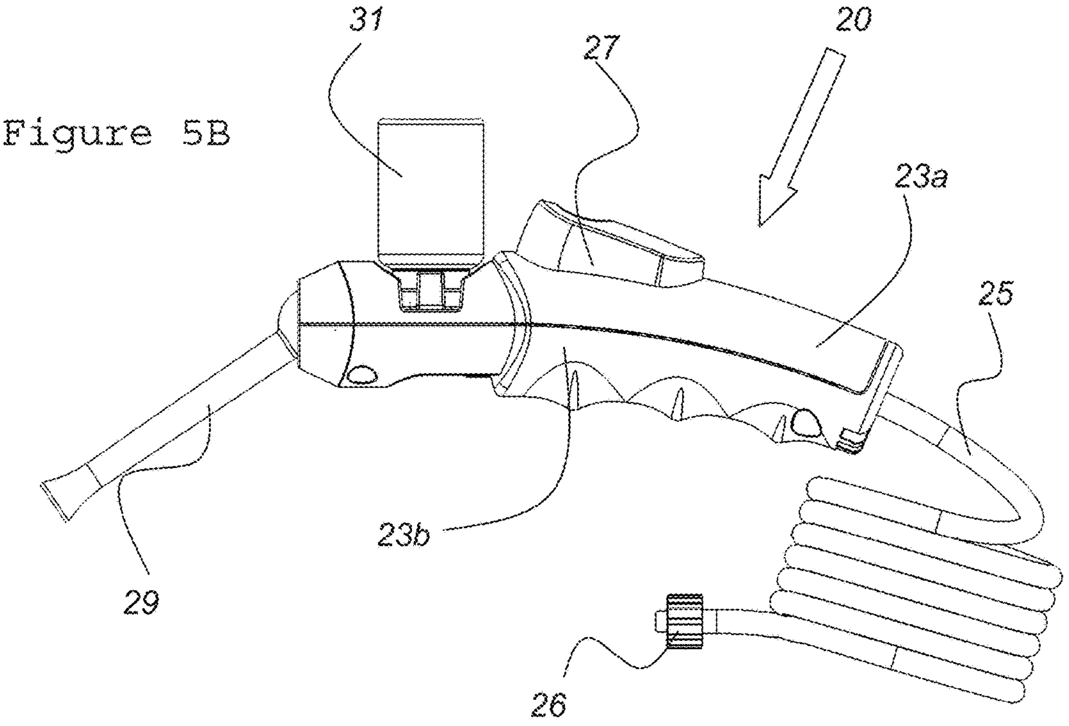
Figure 6A:
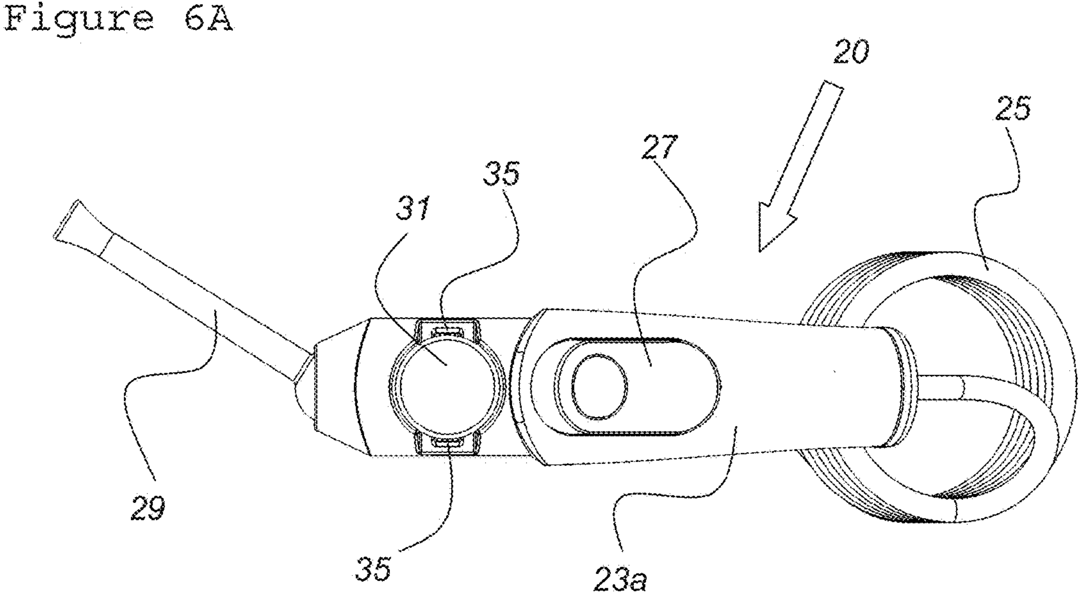
FIGS. 6(*a*) and 6(*b*) illustrate the range of lateral movement of the barrel.
Figure 6B:
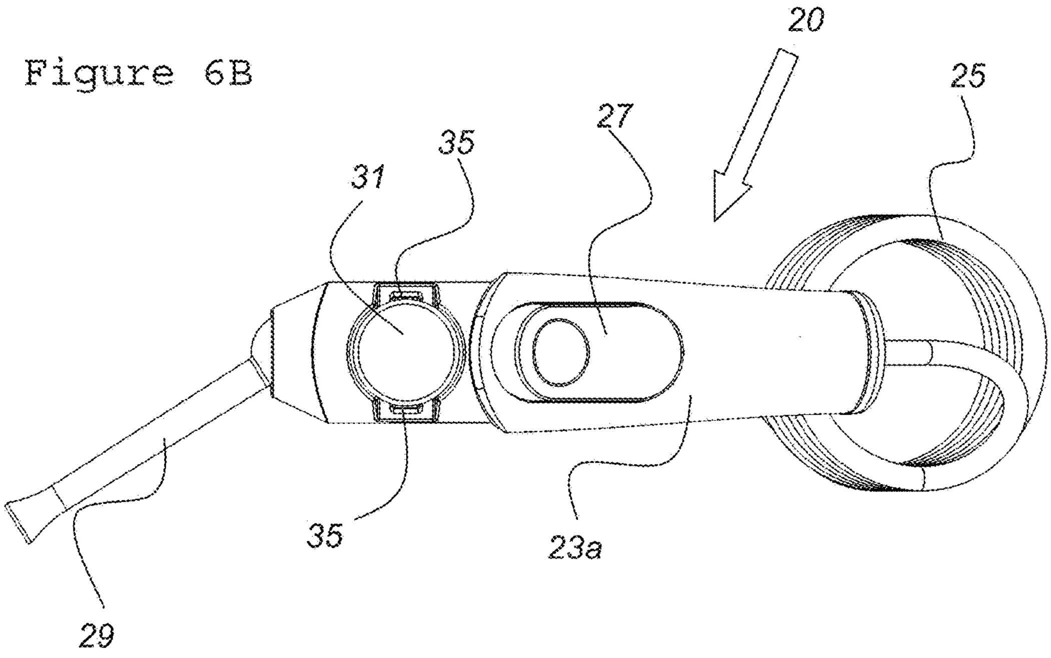

In this embodiment, directional control over the emitted powder is achieved by virtue of the fact that the ball-type connector 291 permits the orientation of the barrel 290 relative to the main body of the device 20 to be varied over a wide range, both vertically (see FIGS. 5(*a*) and 5(*b*)) and laterally (FIGS. 6(*a*) and 6(*b*)).

Figure 7:
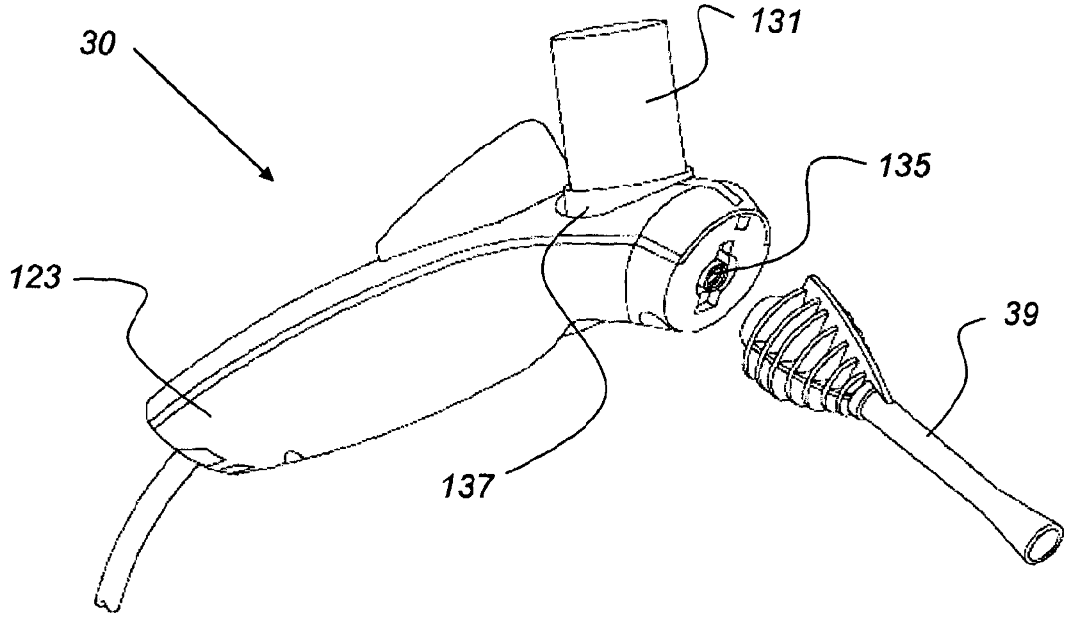
FIG. 7 is a perspective view of a second embodiment of a powder delivery device according to the invention, showing the barrel separated from the main body of the device.

Turning now to FIG. 7, a second embodiment of a powder delivery device according to the invention is generally designated 30. The device 30 is broadly similar to the first embodiment 20 described above in that it comprises a main body 123 that receives vial 131 of powder. In this embodiment, the vial 131 is received within a ring 137 of thermoplastic elastomer that is molded onto the upper component of the main body 123 in a two-shot molding process.

Like the first embodiment 20, the device 30 comprises a tubular outlet barrel 39. In the second embodiment 30, however, the barrel 39 connects to the main body 123 by means of a bayonet fitting and has a fixed orientation relative to the main body 123.

Figure 8:
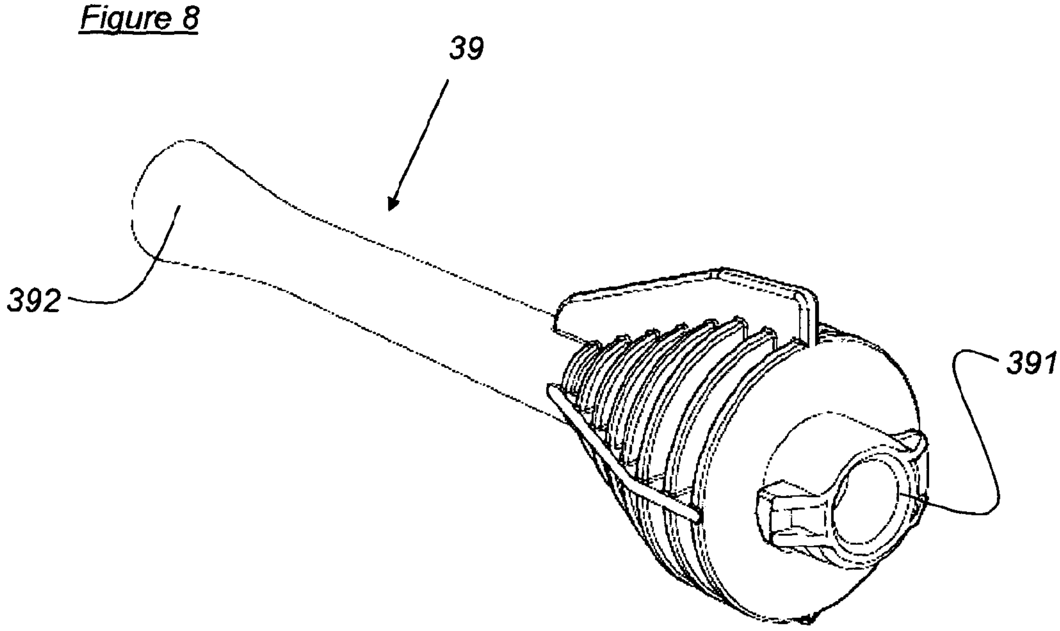
FIG. 8 is a perspective view from behind of the barrel of the device of FIG. 7.
Figure 9:
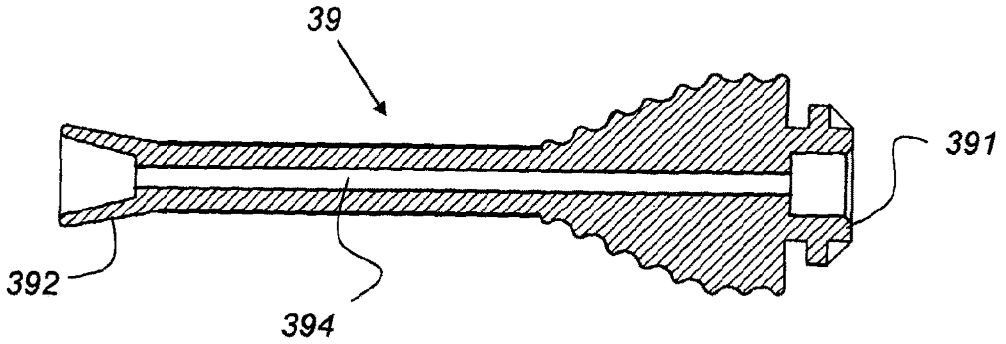
FIG. 9 is a cross-sectional view of the barrel of FIG. 8.

As can be seen in FIG. 8, the face of the barrel that abuts the main body 123 is formed with a male bayonet spigot 391 with a central recess that receives the open end of a tube 135 (see FIG. 7) by which the gasflow and entrained powder are fed from the main body 123 of the device to the barrel 39. The barrel 39 is injection moulded in rigid plastics material (eg ABS) and (referring to FIG. 9), like the barrel 29 of the first embodiment 20, is formed with an internal bore 394 that diminishes along its length (in this case from an internal diameter of approximately 2.9 mm to an internal diameter of approximately 2 mm). The barrel 39 has a flared outlet 392.

As for the first embodiment 20, the narrowing of the main bore 394 may cause an increase in velocity of the gasflow as it exits the device 30 and, together with the flared form of the outlet 392, this may help to maintain the shape of the powder plume emitted from the device 30, resulting in good coverage of the application site with powder. Fall off of powder from the emitted plume, under the influence of gravity, may be reduced, minimising the amount of powder that is dispensed onto sites other than to which the powder is intended to be delivered. The flared form of the outlet 392 also leads to a reduced likelihood of clogging.

Figure 10:
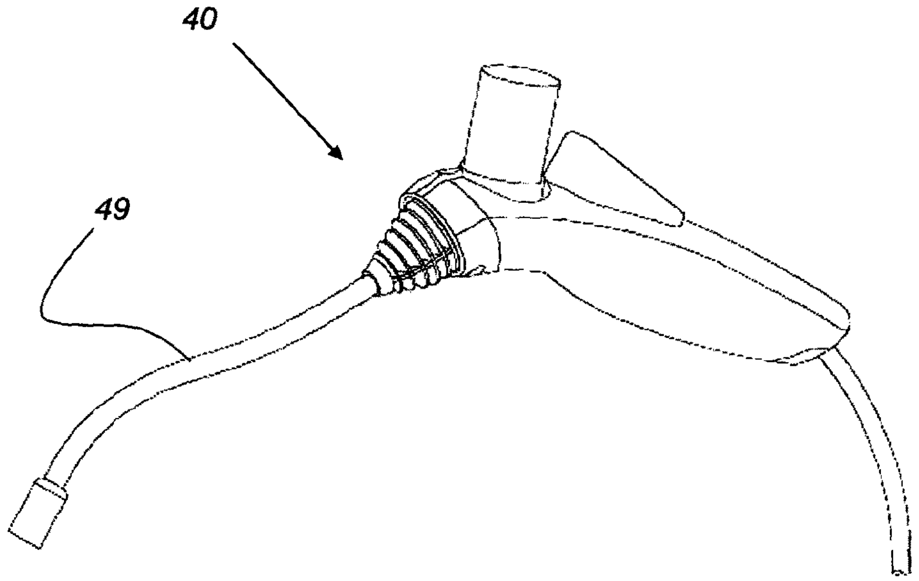
FIG. 10 is a perspective view of a third embodiment of a powder delivery device according to the invention, comprising the main body of the second embodiment with an alternative form of barrel attached to it.

Finally, FIG. 10 depicts a third embodiment of a powder delivery device according to the invention, which is generally designated 40. This embodiment differs from the second embodiment 30 solely in the form of the outlet barrel 49. Indeed, the outlet barrel 39 of the second embodiment 30 and the outlet barrel 49 of the third embodiment 40 are interchangeable.

Figure 11:
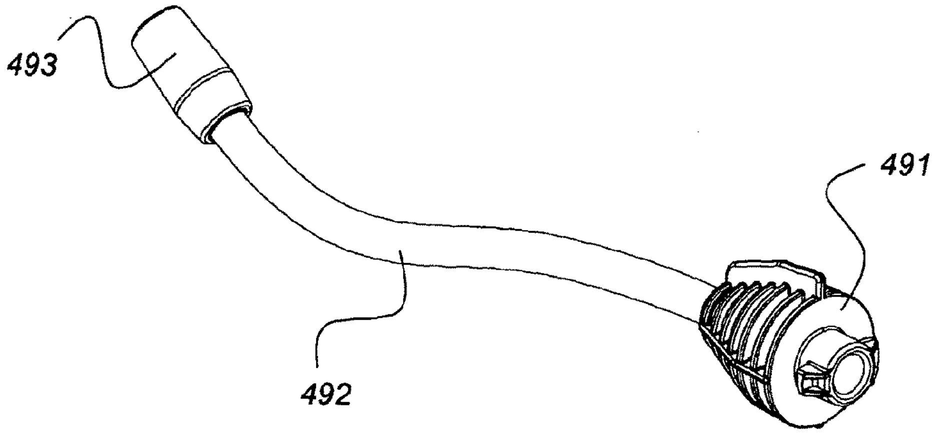
FIG. 11 is a perspective view of the barrel shown in FIG. 10.
Figure 12:
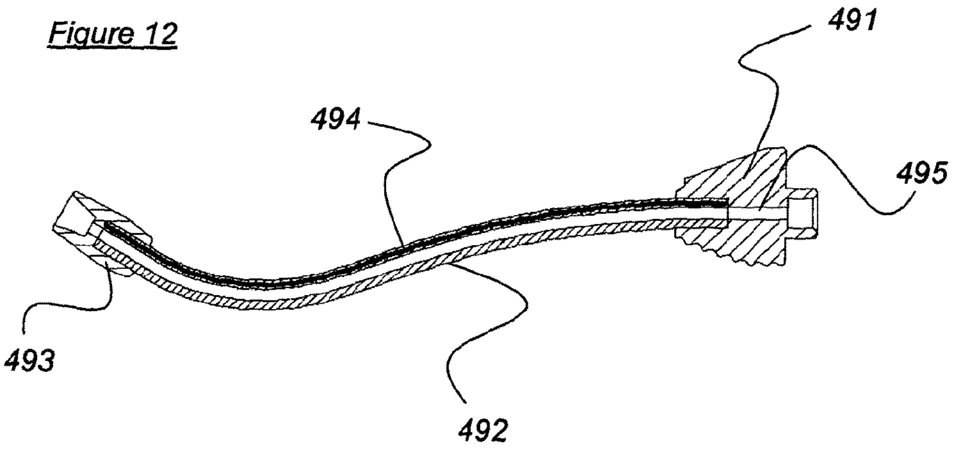
FIG. 12 is a cross-sectional view of the barrel of FIG. 11.

The form of the barrel 49 is shown in greater detail in FIGS. 11 and 12. The barrel 49 comprises three components: a bayonet hub 491, a flexible plastics tube 492 and an outlet tip 493.

The bayonet hub 491 is injection moulded in rigid plastics material (e.g., polyamide) and corresponds in overall shape to the proximal end of the rigid barrel 39 of the second embodiment 30. It has a central bore 495 that terminates in a socket within which one end of the flexible tube 492 is received. That end of the tube 492 may be fixed to the hub 491 by adhesive, by ultrasonic welding or by any other suitable means. The other end of the tube 492 is received within a similar socket formed in the outlet tip 493 (which is also formed by injection moulding of a suitable material, e.g., polyamide) and may be fixed by similar means. The distal (downstream) part of the outlet tip 493 has a flared internal bore.

The flexible tube 492 is formed by extrusion in polyurethane, a copper-coated steel wire 494 being embedded in the wall of the flexible tube 492 during manufacture. A user of the device may therefore form the flexible tube 492 into a desired configuration, the effect of the wire 494 being to retain the tube 492 in that configuration during use. The third embodiment 40 may be particularly useful in surgical procedures in which it is desired to deposit the powder onto surfaces that are hidden and at which a straight barrel cannot be directed.

The invention claimed is:

1. A method of delivering a haemostatic composition to an internal tissue exposed during surgical procedures or after traumatic injury, the method comprising:

providing a device for the dispensing of powder, the device comprising:

a barrel comprising:

a bore including a main portion with a continuous internal surface through which a generated gas flow entrains the powder to be dispensed, and an outwardly flared outlet portion having an internal diameter and an external diameter, wherein:

a length of the main portion is at least fifteen times a maximum internal diameter of the bore;

the internal diameter and external diameter of the outlet portion increases from an upstream end to a downstream end of the outlet portion;

the maximum internal diameter of the main portion is from 1 mm to 6 mm; and the device is charged with a quantity of a haemostatic composition in dry powder form, and dispensing the composition from the device onto the tissue.

2. The method of claim 1, wherein the internal bore of the main portion is tapered.

3. The method of claim 1, wherein the barrel is rigid.

4. The method of claim 3, wherein the length of the main portion of the barrel is at least eighteen times or at least twenty times the maximum internal diameter of the bore.

5. The method of 3, wherein the length of the main portion is between about 30 mm and 100 mm.

6. The method of claim 1, wherein the barrel is flexible.

7. The method of claim 6, wherein the main portion of the barrel has a length of between 50 mm and 300 mm.

8. The method of claim 6, wherein the internal diameter of the barrel is between 1 mm and 5 mm.

9. The method of claim 6, wherein the main portion of the barrel comprises a plastic tube.

10. The method of claim 9, wherein the barrel incorporates one or more malleable elongate members.

11. The method of claim 10, wherein the elongate malleable members are wires or rods.

12. The method of claim 11, wherein the wires or rods are embedded in the plastic material from which the barrel is formed.

13. The method of claim 11, wherein the one or more elongate malleable members are one or more copper or copper-coated steel wires.

14. The method of claim 1, wherein the internal diameter of the main portion decreases from an upstream end to a downstream end of the main portion.

15. The method of claim 1, wherein the internal diameter of the main portion increases from an upstream end to a downstream end of the main portion.

16. The method of claim 1, wherein the internal diameter of the main portion increases from an upstream end to a downstream end of the main portion or decreases from the upstream end to the downstream end of the main portion at a taper angle of 0.5° to 3°.

17. The method of claim 1, wherein the outlet portion has a length of between 5 mm and 25 mm.

18. The method of claim 17, wherein the internal diameter of the outlet portion increases from the upstream end to the downstream end by a factor of two or more.

19. The method of claim 1, wherein the barrel is provided with a mounting that enables an orientation relative to the main portion of the device of which it forms part to be varied.

20. The method of claim 19, wherein the mounting is a ball-and-socket connector.

* * * * *